(12) United States Patent
Dall'occo et al.

(10) Patent No.: US 6,433,203 B1
(45) Date of Patent: Aug. 13, 2002

(54) BRIDGED METALLOCENES, PREPARATION, USE IN CATALYTIC SYSTEMS

(75) Inventors: Tiziano Dall'occo, Ferrara (IT); Vu Anh Dang, Bear; Lin-Chen Yu, Hockessin, both of DE (US); Luigi Resconi; Davide Balboni, both of Ferrara (IT); Alessia Boscarato, Ambrogio (IT); Colin Schaverien, Amsterdam (NL)

(73) Assignee: Basell Technology Company BV (NL)

( * ) Notice: Subject to any disclaimer, the term of this patent is extended or adjusted under 35 U.S.C. 154(b) by 0 days.

(21) Appl. No.: 09/600,351

(22) PCT Filed: Nov. 3, 1999

(86) PCT No.: PCT/EP99/08378
§ 371 (c)(1),
(2), (4) Date: Jul. 14, 2000

(87) PCT Pub. No.: WO00/31088
PCT Pub. Date: Jun. 2, 2000

(30) Foreign Application Priority Data

Nov. 20, 1998 (EP) ............................................. 98203912

(51) Int. Cl.[7] ............................ C07F 17/00; B01J 31/00
(52) U.S. Cl. ........................... 556/11; 556/12; 556/53; 556/43; 556/58; 534/15; 502/103; 502/117; 526/126; 526/160; 526/943
(58) Field of Search ...................... 556/53, 11, 12; 534/15; 502/103, 117; 526/126, 160, 943

(56) References Cited

U.S. PATENT DOCUMENTS

| | | | |
|---|---|---|---|
| 5,086,134 A | 2/1992 | Antberg et al. | 526/126 |
| 5,744,415 A | 4/1998 | Wenzel | 502/121 |
| 5,753,578 A * | 5/1998 | Santi et al. | 502/114 |

FOREIGN PATENT DOCUMENTS

| | | |
|---|---|---|
| DE | 3836059 | 5/1990 |
| DE | 19823168 | 11/1999 |
| EP | 0129368 | 12/1984 |
| EP | 0399348 | 11/1990 |
| EP | 0429320 | 12/1991 |
| EP | 0821011 | 1/1998 |
| JP | 01036606 | 2/1989 |
| JP | 01038408 | 2/1989 |

OTHER PUBLICATIONS

W. Herrmann et al.; Angew. Chem. Int. Ed. Engl. 28 (1989) No. 11.
A. Steinhorst et al., J. Organomet. Chem. (1997) 542(2) 191–204.
H. Urabe et al., Tetrahedron Lett. (1995) 36(31) 5595–98.
T. Hollis et al., Organometallics (1992) 11(8) 2812–16.

* cited by examiner

Primary Examiner—Porfirio Nazario-Gonzalez

(57) ABSTRACT

Metallocene compounds having the general formula (I):

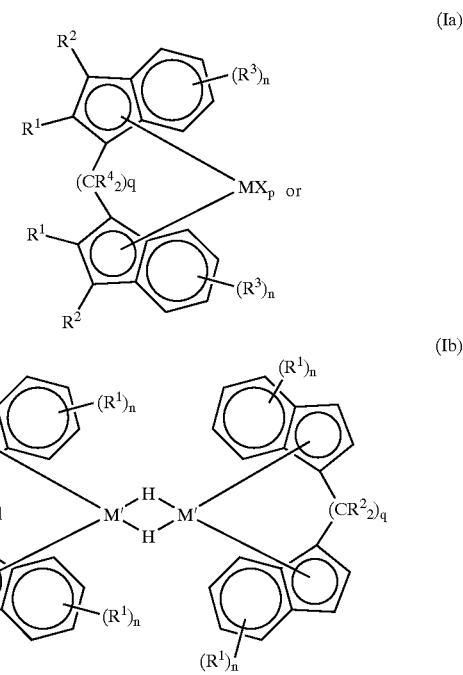

$R^1$ are hydrocarbon groups,
$R^2$ are hydrogen or hydrocarbon groups;
M is a transition metal of group 3, 4, 5, 6 or to the lanthanide or actinide groups in the Periodic Table;
M' is a transition metal selected from those belonging to group 3 or to the lanthanide or actinide groups in the Periodic Table;
X is a monoanionic ligand;
p is an integer of from 0 to 3, being equal to the oxidation state of M minus two;
q is an integer from 3 to 5; and
n is an integer from 1 to 4, when the six-membered rings of formula (Ia) are not perhydrated, and is an integer of from 0 to 4, when the six-membered rings of formula (Ia) are perhydrated as well as in the compound of formula (Ib).

35 Claims, No Drawings

BRIDGED METALLOCENES, PREPARATION, USE IN CATALYTIC SYSTEMS

FIELD OF THE INVENTION

The present invention relates to a new class of metallocene compounds, to a catalyst for the polymerisation of olefins containing them and to a polymerisation process carried out in the presence of said catalyst. The invention also relates to the corresponding ligands useful as intermediates in the synthesis of said metallocene compounds, as well as to processes for preparing said ligands and said metallocene compounds.

DESCRIPTION OF THE PRIOR ART

Metallocene compounds with two cyclopendadienyl groups are known as catalyst components for the polymerisation of olefins.

European Patent 0 129 368, for instance, describes the polymerisation of olefins in the presence of a bis-cyclopentadienyl co-ordination complex containing a transition metal. The two cyclopentadienyl groups can be linked by a bridging group, which is generally a divalent radical containing one or more carbon atoms or heteroatoms.

Also known are bridged metallocene compounds wherein the cyclopentadienyl moiety is condensed to one aromatic or non aromatic ring, the cyclopentadienyl moieties being linked by an ethylene bridge.

For example, European Patent Application EP-0 891 011 describes a process for the preparation of ethylene-based polymers in the presence of ethylenebis(4,7-dimethyl-1-indenyl)zirconium dichloride. The polymers obtained are endowed with low molecular weight. Moreover, the manufacture of ethylene-bridged metallocenes involves the use of the carcinogenic 1,2-dibromoethane.

As regards metallocenes having two equally substituted indenyl groups linked by a bridging group longer than two carbon atoms, only a few compounds have been disclosed.

For example, EP-A-0 399 348 and EP-A-0 459 320 describe the polymerisation of ethylene in the presence of propylenebis(1-indenyl)zirconium dichloride. Although the polyethylene obtained has industrially acceptable molecular weight, the metallocene used in the polymerisation process has low polymerisation activity.

W. A. Herrmann et al. in Angew. Chem. Int. Ed. Engl. 28 (1989), No. 11, describes the use of metallocenes containing two indenyl groups linked by a 1,2-bis(dimethylsilyl)ethane group for the polymerisation of olefins. Although completely inactive toward propylene, an activity toward ethylene was observed. However, there are no data reported about the molecular weight of the polymers.

It would be desirable to find carbon-bridged metallocenes which, when used in catalysts for the polymerisation of olefins, are suitable for the preparation of polyolefins, with the advantage of having higher polymerisation activities and of yielding polymers having improved molecular weights. It would also be desirable to avoid using the carcinogenic 1,2-dibromoethane used for the preparation of metallocenes.

A novel class of metallocene compounds has now unexpectedly been found which has two identical indenyl ligands which are linked to one another by a bridging group longer than an ethylene radical and which can advantageously be used as catalyst components for the polymerisation of olefins.

According to a first aspect, the present invention provides a metallocene compound of the formula (Ia):

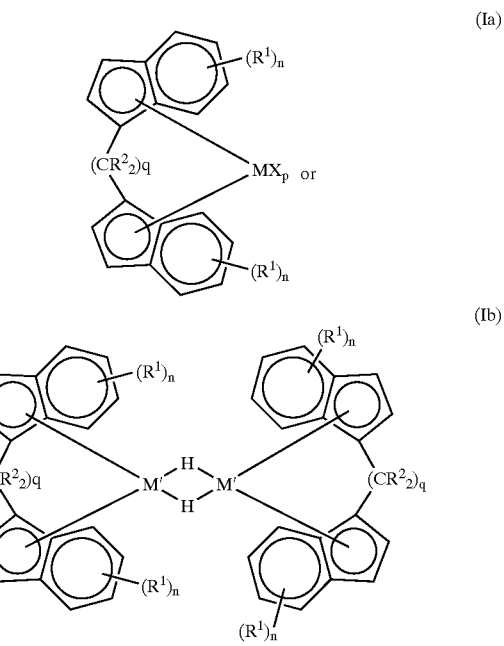

wherein $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;

$R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl, $NR^3_2$, $PR^3_2$, $AsR^3_2$, $OR^3$, $SR^3$ or $SeR^3$ radicals, optionally containing silicon, germanium or halogen atoms; and optionally two adjacent $R^2$ or $R^3$ substituents can form a ring comprising from 5 to 8 carbon atoms;

M is an atom of a transition metal selected from those belonging to group 3, 4, 5, 6 or to the lanthanide or actinide groups in the Periodic Table of the Elements (new IUPAC version), M' is an atom of a transition metal selected from those belonging to group 3 or to the lanthanide or actinide groups in the Periodic Table of the Elements (new IUPAC version), X, same or different, is a monoanionic ligand, such as a hydrogen atom, a halogen atom, an $R^4$, $OR^4$, $OSO_2CF_3$, $OCOR^4$, $SR^4$, $NR^4_2$ or $PR^4_2$ group, wherein the substituents $R^4$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing silicon or germanium atoms;

and optionally the six-membered rings of the compounds of formula (Ia) and (Ib) are perhydrated;

q is an integer from 3 to 5;

n is an integer from I to 4. when the six-membered rings of the compound of formula (Ia) are not perhydrated, and is an integer of from 0 to 4, when the six-membered rings of the compound of formula (Ia) are perhydrated as well as in the compound of formula (Ib);

p is an integer from 0 to 3, being equal to the oxidation state of the metal M minus two.

The transition metal M in compound of formula (Ia) is preferably selected from the group consisting of titanium, zirconium, hafnium, yttrium and scandium.

Non limiting examples belonging to this class are:
1,3-propandiylbis(4-methyl-1-indenyl)zirconium dichloride and dimethyl,
1,3-propandiylbis(5-methyl-1-indenyl)zirconium dichloride and dimethyl,
1,3-propandiylbis(6-methyl-1-indenyl)zirconium dichloride and dimethyl,
1,3-propandiylbis(4,7-dimethyl-1-indenyl)zirconium dichloride and dimethyl,
1,4-butandiylbis(4,7-dimethyl-1-indenyl)zirconium dichloride and dimethyl,
1,5-pentandiylbis(4,7-dimethyl-1-indenyl)zirconium dichloride and dimethyl,
1,6-hexandiylbis(4,7-dimethyl-1-indenyl)zirconium dichloride and dimethyl,
1,3-propandiylbis(4,7-diethyl-1-indenyl)zirconium dichloride and dimethyl,
1,4-butandiylbis(4,7-diethyl-1-indenyl)zirconium dichloride and dimethyl,
1,5-pentandiylbis(4,7-diethyl-1-indenyl)zirconium dichloride and dimethyl,
1,6-hexandiylbis(4,7-diethyl-1-indenyl)zirconium dichloride and dimethyl,
1,3-propandiylbis(4,7-diisopropyl-1-indenyl)zirconium dichloride and dimethyl,
1,4-butandiylbis(4,7-diisopropyl-1-indenyl)zirconium dichloride and dimethyl,
1,5-pentandiylbis(4,7-diisopropyl-1-indenyl)zirconium dichloride and dimethyl,
1,6-hexandiylbis(4,7-diisopropyl-1-indenyl)zirconium dichloride and dimethyl,
1,3-propandiyl(4,7-diisopropyl-1-indenyl)(4-isopropyl-1-indenyl)zirconium dichloride and dimethyl,
1,4-butandiyl(4,7-diisopropyl-1-indenyl)(4-isopropyl-1-indenyl)zirconium dichloride and dimethyl,
1,5-pentandiyl(4,7-diisopropyl-1-indenyl)(4-isopropyl-1-indenyl)zirconium dichloride and dimethyl,
1,6-hexandiyl(4,7-diisopropyl-1-indenyl)(4-isopropyl-1-indenyl)zirconium dichloride and dimethyl,
1,3-propandiylbis(4,7-dimethyl-1-tetrahydroindenyl)zirconium dichloride and dimethyl,
1,3-propandiylbis(1-tetrahydroindenyl)zirconium dichloride and dimethyl,
1,4-butandiylbis(4,7-dimethyl-1-tetrahydroindenyl)zirconium dichloride and dimethyl,
1,4-butandiylbis(1-tetrahydroindenyl)zirconium dichloride and dimethyl,
1,5-pentandiylbis(4,7-dimethyl-1-tetrahydroindenyl)zirconium dichloride and dimethyl,
1,5-pentandiylbis(1-tetrahydroindenyl)zirconium dichloride and dimethyl,
1,6-hexandiylbis(4,7-dimethyl-1-tetrahydroindenyl)zirconium dichloride and dimethyl,
1,6-hexandiylbis(1-tetrahydroindenyl)zirconium dichloride and dimethyl,
1,3-propandiylbis(4,7-diethyl-1-tetrahydroindenyl)zirconium dichloride and dimethyl,
1,4-butandiylbis(4,7-diethyl-1-tetrahydroindenyl)zirconium dichloride and dimethyl,
1,5-pentandiylbis(4,7-diethyl-1-tetrahydroindenyl)zirconium dichloride and dimethyl,
1,6-hexandiylbis(4,7-diethyl-1-tetrahydroindenyl)zirconium dichloride and dimethyl,
1,3-propandiylbis(4,7-diisopropyl-1-tetrahydroindenyl)zirconium dichloride and dimethyl,
1,4-butandiylbis(4,7-diisopropyl-1-tetrahydroindenyl)zirconium dichloride and dimethyl,
1,5-pentandiylbis(4,7-diisopropyl-1-tetrahydroindenyl)zirconium dichloride and dimethyl,
1,6-hexandiylbis(4,7-diisopropyl-1tetrahydroindenyl)zirconium dichloride and dimethyl,
1,3-propandiylbis(4,7-ditrimethylsilyl-1-tetrahydroindenyl)zirconium dichloride and dimethyl,
1,4butandiylbis(4,7-ditrimethylsilyl-1-tetrahydroindenyl)zirconium dichloride and dimethyl,
1,5-pentandiylbis(4,7-ditrimethylsilyl-1-tetrahydroindenyl)zirconium dichloride and dimethyl,
1,6-hexandiylbis(4,7-ditrimethylsilyl-1-tetrahydroindenyl)zirconium dichloride and dimethyl,
1,3-propandiylbis(4-methyl-1-indenyl)yttrium bistrimethylsilylmethyl,
1,3-propandiylbis(5-methyl-1-indenyl)yttrium bistrimethylsilylmethyl,
1,3-propandiylbis(6-methyl-1-indenyl)yttrium bistrimethylsilylmethyl,
1,3-propandiylbis(4,7-dimethyl-1-indenyl)yttrium bistrimethylsilylmethyl,
1,4-butandiylbis(4,7-dimethyl-1-indenyl)yttrium bistrimethylsilylmethyl,
1,5-pentandiylbis(4,7-dimethyl-1-indenyl)yttrium bistrimethylsilylmethyl,
1,6-hexandiylbis(4,7-dimethyl-1-indenyl)yttrium bistrimethylsilylmethyl,
1,3-propandiylbis(4,7-dimethyl-1-indenyl)scandium bistrimethylsilylmethyl,
1,4-butandiylbis(4,7-dimethyl-1-indenyl)scandium bistrimethylsilylmethyl,
1,5-pentandiylbis(4,7-dimethyl-1-indenyl)scandium bistrimethylsilylmethyl,
1,6-hexandiylbis(4,7-dimethyl-1-indenyl)scandium bistrimethylsilylmethyl,
1,3-propandiyl(4,7-dimethyl-1-indenyl)(4-methyl-1-indenyl)scandium bistrimethylsilylmethyl,
1,4-butandiyl(4,7-dimethyl-1-indenyl)(4-methyl-1-indenyl)scandium bistrimethylsilylmethyl,
1,5-pentandiyl(4,7-dimethyl-1-indenyl)(4-methyl-1-indenyl)scandium bistrimethylsilylmethyl,
1,6hexandiyl1(4,7-dimethyl-1-indenyl)(4-methyl-1-indenyl)scandium bistrimethylsilylmethyl Non-limiting examples belonging to the class of compounds of formula (Ib) are:
di[1,3-propandiylbis(4,7-dimethyl-1-indenyl)yttrium hydride];
di[1,4-butandiylbis(4,7-dimethyl-1-indenyl)yttrium hydride];
di[1,5-pentandiylbis(4,7-dimethyl-1-indenyl)yttrium hydride];
di[1,6-hexandiylbis(4,7-dimethyl-1-indenyl)yttrium hydride];
di[1,3-propandiylbis(4,7-dimethyl-1-indenyl)scandium hydride];
di[1,4-butandiylbis(4,7-dimethyl-1-indenyl)scandium hydride];
di[1,5-pentandiylbis(4,7-dimethyl-1-indenyl)scandium hydride];
di[1,6-hexandiylbis(4,7-dimethyl-1-indenyl)scandium hydride];
di[1,3-propandiyl(4,7-dimethyl-1-indenyl)(4-methyl-1-indenyl)scandium hydride];
di[1,4-butandiyl(4,7-dimethyl-1-indenyl)(4-methyl-1-indenyl)scandium hydride];
di[1,5-pentandiyl(4,7-dimethyl-1-indenyl)(4-methyl-1-indenyl)scandium hydride];

di[1,6-hexandiyl(4,7-dimethyl-1-indenyl)(4-methyl-1-indenyl)scandium hydride].

A particularly interesting class of metallocenes according to the invention is that of the compounds of the formula (Ia), wherein the transition metal M is zirconium, the X substituents are chlorine atoms or methyl groups, the substituents $R^2$ are hydrogen atoms and q is 3. Still particularly preferred are those compounds in which n is 2 and the two $R^1$ substituents are in position 4 and 7 on the indenyl moieties.

Non limiting examples of that class are:
1,3-propandiylbis(4,7-dimethyl-1-indenyl)zirconium dichloride and dimethyl,
1,3-propandiylbis(4,7-diethyl-1-indenyl)zirconium dichloride and dimethyl,
1,3-propandiylbis(4,7-diisopropyl-1-indenyl)zirconium dichloride and dimethyl,
1,3-propandiylbis(4,7ditertbutyl-1-indenyl)zirconium dichloride and dimethyl,
1,3-propandiylbis(4,7-di-n-butyl-1-indenyl)zirconium dichloride and dimethyl,
1,3-propandiylbis(4,7-dicyclopropyl-1-indenyl)zirconium dichloride and dimethyl,
1,3-propandiylbis(4,7-dicyclobutyl-1-indenyl)zirconium dichloride and dimethyl,
1,3-propandiylbis(4,7-dicyclopentyl-1-indenyl)zirconium dichloride and dimethyl,
1,3-propandiylbis(4,7-dicyclohexyl-1-indenyl)zirconium dichloride and dimethyl,
1,3-propandiylbis(4,7-diphenyl-1-indenyl)zirconium dichloride and dimethyl,
1,3-propandiylbis(4,7-ditrimethylsilyl-1-indenyl)zirconium dichloride and dimethyl,
1,3-propandiylbis(4,7-ditrimethylgermilyl-1-indenyl)zirconium dichloride and dimethyl.

According to another aspect of the present invention there is provided a class of ligands of formula (II):

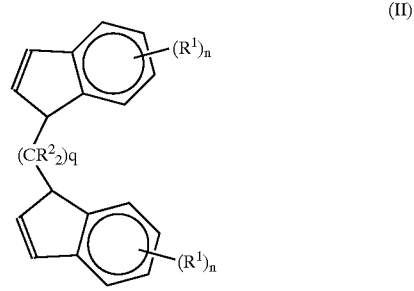

(II)

wherein
$R^1$, $R^2$, n and q have the meaning as reported above.

The two double bonds of the cyclopentadienyl ring of the ligands of formula (II) can be in any of the allowed positions.

The aforementioned compounds of formula (II) are particularly useful as ligands for the preparation of the metallocene compounds of formula (Ia) and (Ib).

An advantageous class of ligands according to the present invention corresponds to formula (II), wherein $R^2$ are hydrogen atoms and q is 3.

Non limiting examples of this class of ligands are:
1,3-propandiylbis(4,7-dimethyl-1-indenyl),
1,3-propandiylbis(4,7-diethyl-1-indenyl),
1,3-propandiylbis(4,7-diisopropyl-1-indenyl),
1,3-propandiylbis(4,7-ditertbutyl-1-indenyl),
1,3-propandiylbis(4,7-di-n-butyl-1-indenyl),
1,3-propandiylbis(4,7-dicyclopropyl-1-indenyl),
1,3-propandiylbis(4,7-dicyclobutyl-1-indenyl),
1,3-propandiylbis(4,7-dicyclopentyl-1-indenyl),
1,3-propandiylbis(4,7-dicyclohexyl-1-indenyl),
1,3-propandiylbis(4,7-ditrimethylsilyl-1-indenyl),
1,3-propandiylbis(4,7-ditrimethylgermyl-1-indenyl).

According to a further aspect of the present invention there is provided a process for the preparation of ligands of formula (II) comprising the following steps:
contacting a compound of formula (III):

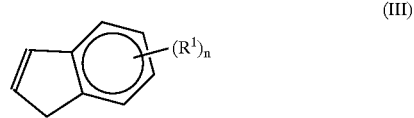

(III)

and its double bond isomers, wherein
$R^1$ and n have the meaning as reported above, with a compound of general formula $(CR^2)_qZ_2$, wherein $R^2$ and q are defined as above, and Z is a halogen atom, in the presence of a base, to form a compound of formula (II).

As to the structural bridge $(CR^2)_q$ in the above ligands, $R^2$ and q have the meaning as defined above.

Non limiting examples of bases used to form the compound of formula (II) are hydroxides and hydrides of alkali- and earth-alkali metals, metallic sodium and potassium and organometallic lithium salts. Preferably, methyllithium or n-butyllithium is used.

Non limiting examples of compounds of general formula $(CR^2)_qZ_2$ are 1,6-dibromohexane, 1,5-dibromopentane, 1,4-dibromobutane and 1,3-dibromopropane. Most preferably, 1,3-dibromopropane is used.

The synthesis of the above bridged ligands of formula (II) is preferably carried out by adding a solution of an organic lithium compound in an apolar solvent to a solution of the compound (III) in an aprotic polar solvent. The thus obtained solution containing the compound (III) in the anionic form is then added to a solution of the compound of formula $(CR^2)_qZ_2$ in an aprotic polar solvent. The bridged ligand can be finally separated by conventional general known procedures.

Not limiting examples of aprotic polar solvents which can be used in the above process are tetrahydrofurane, dimethoxyethane, diethylether, toluene and dichloromethane. Not limiting examples of apolar solvents suitable for the above process are pentane, hexane and benzene.

During the whole process, the temperature is preferably kept between −180° C. and 80° C., and more preferably between −20° C. and 40° C.

A still further aspect of the present invention is a process for the preparation of the metallocene compounds of formula (Ia), obtainable by contacting the ligand of formula (II) as described above, with a compound capable of forming a corresponding dianionic compound thereof and thereafter smith a compound of formula $MX_{p+2}$, wherein M, X and p have the meanings as defined above.

The compound able to form said dianion is selected from the group consisting of hydroxides and hydrides of alkali- and earth-alkali metals, metallic sodium and potassium, and organometallic lithium salts, and preferably said anion is n-butyllithium.

Non-limiting examples of compounds of formula $MX_{p+2}$ are titanium tetrachloride, zirconium tetrachloride and hafnium tetrachloride. Preferably, zirconium tetrachloride is used.

The metallocene compounds of formula (Ia) can be prepared by first reacting the bridged ligands of formula (II), prepared as described above, with a compound able to form a delocalized anion on the cyclopentadienyl rings, and thereafter with a compound of formula $MX_{p+2}$, wherein M and the substituents X are defined as above.

More specifically, said bridged ligands of formula (II) are dissolved in an aprotic polar solvent and to the obtained solution is added a solution of an organic lithium compound in an apolar solvent. The thus obtained anionic form is separated, dissolved in an aprotic polar solvent and thereafter added to a suspension of the compound $MX^{p+2}$ in an aprotic polar solvent. At the end of the reaction, the solid product obtained is separated from the reaction mixture by techniques commonly used in the state of the art. Non limiting examples of aprotic polar solvents suitable for the above reported processes are tetrahydrofurane, dimethoxyethane, diethylether, toluene and dichloromethane. Non limiting examples of apolar solvents suitable for the above process are pentane, hexane and benzene.

During the whole process, the temperature is preferably kept between −80° C. and 80° C., and more preferably between −20° C. and 40° C.

A particularly convenient method for preparing the metallocene compounds of formula (Ia) and (Ib), in which the two six-membered rings of the indenyl groups are perhydrated, i.e. all carbon atoms of the six-membered ring of the indenyl radical are saturated, is the hydrogenation reaction of the corresponding metallocene compounds in which both indenyl groups are selected from the groups of formula (III). The hydrogenation reaction is carried out in a solvent, such as $CH_2Cl_2$, in the presence of a hydrogenation catalyst, such as $PtO_2$, and hydrogen. The hydrogen pressures are preferably comprised between 1 and 100 bar, and the temperatures are preferably comprised between −50 and 50° C.

When at least one X substituent in the metallocene compound of formula (I) is different from halogen, it is necessary to substitute at least one substituent X in the obtained metallocene with at least another substituent different from halogen. Such a substitution reaction is carried out by methods known in the state of the art. For example, when the substituents X are alkyl groups, the metallocenes can be reacted with alkylmagnesium halides (Grignard reagents) or with lithiumalkyl compounds.

According to another embodiment, when in formula (Ia) the X groups have the meaning of —$R^4$, as defined above, the metallocenes of the invention can be obtained by reacting directly a ligand of formula (II) with at least one molar equivalent of a compound of formula $MX_s$, in the presence of at least (p+2) molar equivalents of a suitable alkylating agent, wherein $R^4$, M and X have the meaning reported above and s is an integer corresponding to the oxidation state of the metal M and ranges from 3 to 6. Said alkylating agent can be an alkaline or alkaline-earth metal, such as $LiR^4$ or $MgR^4_2$, or a Grignard reagent, such as $R^4MgCl$ or $R^4MgBr$, as described in WO 99/36427.

During the whole process, the temperature is preferably kept between −180° C. and 80° C., and more preferably between −20° C. and 40° C.

According to a still further aspect of the present invention it is provided a process for the preparation of metallocene compounds of formula (Ib), comprising the following steps:
a) contacting a compound of formula (II) as defined above with a base selected from hydroxides and hydrides of alkali- and earth alkali metals, metallic sodium and potassium and organic lithium compounds, wherein the mole ratio between said base and the compound of formula (II) is at least 2.
b) contacting the product obtained under a) with a compound of formula (IV) $M'X_3$, M' being defined as above, and X is a halogen atom, in the presence of a polar aprotic solvent selected from dimethoxyethane, diethylether, tetrahydrofurane, toluene and dichloromethane;
c) treating the obtained product with a compound of formula $M''CH(TMS)_2$ (TMS=trimethylsilyl), M'' being an alkali metal, and subsequent
d) treating the product of step c) in a stream of hydrogen.

Preferably the base as used in step a) is n-butyllithium. More specifically, said bridged ligands of formula (II) are dissolved in an aprotic polar solvent and to the obtained solution is added a solution of an organic lithium compound in an apolar solvent. The thus obtained anionic form is separated, dissolved in an aprotic polar solvent and thereafter added to a suspension of the compound $M'X_3$ in an aprotic polar solvent. At the end of the reaction, the solid product obtained is separated from the reaction mixture by techniques commonly used in the state of the art. Non limiting examples of aprotic polar solvents suitable for the above reported processes are tetrahydrofurane, dimethoxyethane, diethylether, toluene and dichloromethane. Preferably the polar aprotic solvent used in step b) is tetrahydrofurane.

Preferably the compound of formula (IV) is $ScCl_3$ or $YCl_3$.

Preferably the compound of formula $M''CH(TMS)_2$ is $LiCH(TMS)_2$, $NaCH(TMS)_2$ and $KCH(TMS)_2$. Most preferably, $LiCH(TMS)_2$ is used.

During the whole process, the temperature is preferably kept between −180° C. and 80° C., and more preferably between −20° C. and 40° C.

The metallocene compounds of the present invention can conveniently be used as catalyst components for the polymerisation of olefins.

Thus, according to a still further aspect of the present invention there is provided a catalyst for the polymerisation of olefins, obtainable by contacting:
(A) a metallocene compound of formula (Ia), and
(B) an alumoxane and/or a compound capable of forming an alkyl metallocene cation.

The alumoxane used as component (B) can be obtained by reacting water with an organo-aluminium compound of formula $AlR^5_3$ or $Al_2R^5_6$, wherein the $R^5$ substituents, same or different from each other, are hydrogen, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl. optionally containing silicon or germanium atoms In this reaction the molar ratio of Al/water is comprised between 1:1 and 100:1.

The molar ratio between aluminium and the metal of the metallocene is comprised between about 10:1 and about 20000:1, and preferably between about 100:1 and about 5000:1.

The alumoxanes used in the catalyst according to the invention are considered to be linear, branched or cyclic compounds containing at least one group of the type:

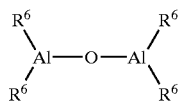

wherein the $R^6$ substituents, same or different, are hydrogen atoms, $C_1$–$C_{20}$-alkyl, $C_3$–$C_{20}$-cyclalkyl, $C_6$–$C_{20}$-aryl, $C_1$–$C_{20}$-alkylaryl or $C_7$–$C_{20}$-arylalkyl, optionally containing silicon or germanium atoms or are a —O—$Al(R^6)_2$ group and, if appropriate, some $R^6$ substituents can be halogen atoms.

In particular. alumoxanes of the formula:

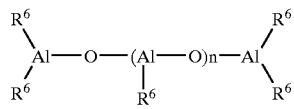

can be used in the case of linear compounds, wherein n is 0 or an integer from 1 to 40 and the $R^6$ substituents are defined as above, or alumoxanes of the formula:

can be used in the case of cyclic compounds, wherein n is an integer from 2 to 40 and the $R^6$ substituents are defined as above.

Examples of alumoxanes suitable for use according to the present invention are methylalumoxane (MAO), tetra-(isobutyl)alumoxane (TIBAO), tetra-(2,4,4-trimethylpentyl) alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 in which the alkyl groups have specific branched patterns.

Non-limiting examples of aluminium compounds according to said PCT application are: tris(2,3,3-trimethyl-butyl) aluminium, tris(2,3-dimethyl-hexyl)aluminium, tris(2,3-dimethyl-butyl)aluminium, tris(2,3-dimethyl-pentyl) aluminium tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl) aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl) aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl -pentyl) aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl) aluminium, tris(2,3-dimethyl-3-phenyl-butyl)aluminium, as well as the corresponding compounds wherein one of the hydrocarbyl groups is replaced by an hydrogen atom, and those wherein one or two of the hydrocarbyl groups are replaced by an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl)aluminium (TDMBA) and tris(2,3,3-trimethylbutyl)aluminium (TTMBA) are preferred.

In the catalyst used in the process according to the invention for the preparation of polyolefins, both the metallocene compound of the formula (Ia) and the alumoxane can be present as the product of the reaction with an organometallic aluminium compound of the formula $AlR^5_3$ or $Al_2R^5_6$, in which the $R^5$ substituents, same or different, are hydrogen atoms, halogen atoms, $C_1$–$C_{20}$-alkyl, $C_3$–$C_{20}$-cyclalkyl, $C_6$–$C_{20}$-aryl, $C_7$–$C_{20}$-alkylaryl or $C_7$–$C_{20}$-arylalkyl, optionally containing silicon or germanium atoms.

Non-limiting examples of aluminium compounds of the formula $AlR^5_3$ or $Al_2R^5_6$ are: $Al(Me)_3$, $Al(Et)_3$, $AlH(Et)_2$, $Al(iBu)_3$, $Al(iHex)_3$, $Al(iOct)_3$, $Al(C_6H_5)_3$, $Al(CH_2C_6H_5)_3$, $Al(CH_2CMe_3)_3$, $Al(CH_2SiMe_3)_3$, $Al(Me)_2iBu$, $Al(Me)_2Et$, $AlMe(Et)_2$, $AlMe(iBu)_2$, $Al(Me)_2iBu$, $Al(Me)_2Cl$, $Al(Et)_2Cl$, $AlEtCl_2$, $Al_2(Et)_3Cl_3$, wherein Me=methyl, Et=ethyl, iBu= isobutyl, iHex=isohexyl, iOct=2,4,4-trimethyl-pentyl.

Non limiting examples of compounds able to form a metallocene alkyl cation are compounds of formula $T^+D^-$, wherein $T^+$ is a Brønsted acid, able to give a proton and to react irreversibly with a substituent L of the metallocene of formula (Ia), and $D^-$ is a compatible anion, which does not co-ordinate, which is able to stabilise the active catalytic species which originates from the reaction of the two compounds and which is sufficiently labile to be able to be removed from an olefinic substrate. Preferably, the anion $D^-$ comprises one or more boron atoms. More preferably, the anion $D^-$ is an anion of the formula $BAr^{(-)}_4$, wherein substituents Ar, the same or different from each other, are aryl radicals such as phenyl, pentafluorophenyl, bis (trifluoromethyl)phenyl. Particularly preferred is the tetrakis-pentafluorophenyl borate. Furthermore, compounds of formula $BAr_3$ can be suitably used.

The catalysts of the present invention are particularly suitable to be supported on inert carriers and used in the process of the present invention. This is obtained by depositing the metallocene (A) or the product of the reaction of the same with the component (B), or the component (B) and thereafter the metallocene (A), on supports such as for example silica, alumina, styrene-divinylbenzene copolymers, polyethylene or polypropylene.

The solid compound so obtained, in combination with further addition of the alkyl aluminium compound as such or pre-reacted with water, is usefully employed in gas phase polymerisation. Catalysts of the present invention are useful in the homo- and copolymerization reaction of olefins.

Therefore, a still further object of the present invention is a process for the polymerisation of olefins comprising the polymerisation reaction of at least an olefinic monomer in the presence of a catalyst as above described.

The catalysts of the present invention can be used in the homo-polymerisation reaction of olefins, preferably of ethylene for the preparation of HDPE. In ethylene polymerisation, the metallocenes of the invention show very good activities even when used in very low Al/Zr ratios.

A particular advantage of the metallocenes of the general formula (Ib) is their direct use in the polymerization process of olefins without the use of a cocatalyst.

Another interesting use of the catalysts according to the present invention is in the copolymerization of ethylene with alpha-olefins, such as propylene and 1-butene. In particular, the catalysts of the invention can be used for the preparation of LLDPE.

Suitable olefins to be used as comonomers comprise α-olefins of the formula $CH_2$=$CHR^7$, wherein $R^7$ is an alkyl radical having from 1 to 10 carbon atoms, and cycloolefins. Examples of these olefins are propylene, 1-butene, 1-pentene, 4-methyl-1-pentene, 1-hexene, 1-octene, 1-decene, 1-dodecene, 1-tetradecene, 1-esadecene, 1-octadecene, 1-eicosene, allylcyclohexene, cyclopentene, cyclohexene, norbornene and 4,6-dimethyl-1 -heptene.

The copolymers may also contain small proportions of units deriving from polyenes, in particular from straight or cyclic, conjugated or non conjugated dienes, such as 1,4-hexadiene, isoprene, 1,3-butadiene, 1,5-hexadiene and 1,6-heptadiene.

The units deriving from a-olefins of formula $CH_2$=$CHR^7$, from cycloolefins and/or from polyenes are present in the copolymers preferably in amounts ranging from 1% to 20% by mole.

The saturated copolymers can contain ethylene units and α-olefins and/or non conjugated diolefins able to cyclopolymerise. The unsaturated copolymers can contain, together with the units deriving from the polymerisation of ethylene and α-olefins, also small proportions of unsaturated units deriving from the copolymerization of one or more polyenes. The content of unsaturated units is preferably comprised between 0 and 5% by weight.

Suitable non conjugated diolefins able to cyclopolymerise comprise 1,5-hexadiene, 1,6-heptadiene and 2-methyl-1,5-hexadiene.

Non limiting examples of suitable polyenes are:
(i) polyenes able to give unsaturated units, such as:
linear, non-conjugated dienes, such as 1,4-hexadiene trans, 1,4-hexadiene cis, 6-methyl-1,5-heptadiene, 3,7-dimethyl-1,6-octadiene and 11-methyl-1,10-dodecadiene;
bicyclic diolefins, such as 4,5,8,9-tetrahydroindene and 6 and 7-methyl-4,5,8,9-tetrahydroindene;
alkenyl or alkyliden norbornenes, such as 5-ethyliden-2-norbornene, 5-isopropyliden-2-norbornene and exo-5-isopropenyl-2-norbornene;
polycyclic diolefins, such as dicyclopentadiene, tricyclo-[6,2,1,0]4,9-undecadiene and the 4-methyl derivative thereof;
(ii) non-conjugated diolefins able to cyclopolymerise, such as 1,5-hexadiene, 1,6-heptadiene and 2-methyl-1,5-hexadiene;
(iii) conjugated dienes, such as butadiene and isoprene.

Polymerisation processes according to the present invention can be carried out in gaseous phase or in liquid phase, optionally in the presence of an inert hydrocarbon solvent either aromatic (such as toluene), or aliphatic (such as propane, hexane, heptane, isobutane and cyclohexane).

The polymerisation temperature is preferably ranging from about 0° C. to about 250° C. In particular, in the processes for the preparation of HDPE and LLDPE, it is preferably comprised between 20° C. and 150° C. and, more preferably between 40° C. and 90° C., whereas for the preparation of the elastomeric copolymers it is preferably comprised between 0C and 200° C. and, more preferably between 20° C. and 100° C.

The polymerisation pressure is ranging from 0,5 to 100 bar, preferably from 2 to 50 bar, and more preferably from 4 to 30 bar.

The molecular weight of the polymers can be also varied merely by varying the polymerisation temperature, the type or the concentration of the catalytic components or by using molecular weight regulators such as, for example, hydrogen.

The molecular weight distribution can be varied by using mixtures of different metallocenes, or carrying out the polymerisation in several steps at different polymerisation temperatures and/or different concentrations of the molecular weight regulator.

The polymerisation yields depend on the purity of the metallocene component of the catalyst. Therefore, in order to increase the yields of polymerisation, metallocenes are generally used after a purification treatment.

The components of the catalyst can be brought into contact before the polymerisation. The pre-contact concentrations are generally between 1 and $10^{-8}$ mol/l for the metallocene component (A), while they are generally between 10 and $10^{-8}$ mol/l for the component (B). The pre-contact is generally effected in the presence of a hydrocarbon solvent and, if appropriate, of small quantities of monomer. The pre-contact time is generally comprised between 1 minute and 24 hours.

The following examples are given to illustrate and not to limit the invention.

General Procedures Characterizations

The following abbreviations are used:
THF=tetrahydrofuran
NaOEt=sodium ethoxide
BuLi=butyllithium
MeOH=methanol
EtOH=ethanol
KH=potassium hydride
TMSCl=trimethylsilylchloride
PBDMI=1,3-bis(4,7-dimethyl-1-indenyl)propane All operations were performed under nitrogen by using conventional Schlenk-line techniques. Solvents were distilled from blue Na-benzophenone ketyl ($Et_2O$), $CaH_2$ ($CH_2Cl_2$) or $AliBu_3$(hydrocarbons). and stored under nitrogen. BuLi (Aldrich) was used as received.

The $^1$H-NMR analyses of the metallocenes were carried out on an AC200 Bruker spectrometer ($CD_2Cl_2$, referenced against the middle peak of the triplet of the residual $CHDCl_2$ at 5.35 ppm). All NMR solvents were dried over $P_2O_5$ and distilled before use. Preparation of the samples were carried out under nitrogen using standard inert atmosphere techniques. The lanthanide hydrades and $CHTMS_2$ alkyls were characterized in $C_6D_6$.

Preparation of the Ligands

Synthesis of α, α'-o-Xylenyl-bis-4,7-dimethylindene

In a 250 ml round-bottom flask supplied with magnetic stirrer and dropping funnel were placed 14.4 g (0.1 mol) of 4,7-dimethylindene and 130 ml of THF. This reaction mixture was cooled down to −78° C. with acetone/dry ice mixture and 62.6 ml of 1.6 molar BuLi solution in hexane were added dropwise. Then, the cooling bath was removed and the temperature of the reaction mixture was slowly elevated until room temperature. The obtained dark colored mixture was transformed into 250 ml dropping funnel and added dropwise during 1 h to the solution of 13.2 g (0.05 mol) of α,α'- dibromoxylene in 100 ml of THF under vigorous stirring. During all the addition procedure the temperature of the reaction mixture was stirred overnight. 10 ml of methanol were added and the solvents were removed under reduced pressure. The resulting solvent was suspended in 100 ml of hexane/CH2Cl2 (4:1) mixture and passed through silica gel using the same mixture as eluent. Then solvents were removed under reduced pressure and the resulting slightly yellow crystalline product was washed twice with small portions of cold ethanol and dried in vacuum. Yield: 78%. Purity: 95.6%. The desired product was determined by $^1$H-NMR spectroscopy.

Preparation of the Metallocenes

The preparation of ethylene-bis(4,7-dimethyl-indenyl) zirconium dichloride $EBDMIZrCl_2$ was carried out according to the method described in the European patent application EP-0 821 011. Ethylen-bis(indenyl)zirconium dichloride $EBIZrCl_2$ was purchased from the Witco company.

EXAMPLE 1

Preparation of rac/meso-1,3-propandiylbis(4,7-dimethyl-1-indenyl)zirconium dichloride (r/m-$PBDMIZrCl_2$)

(1a) Synthesis of 1,3-bis(4,7-dimethyl-1-indenyl)propane 31 mL of BuLi 2.5 M in hexane (76 mmol) were added dropwise to a solution of 4,7-dimethylindene (10.00 g, 69 mmol) in THF (30 mL) at −78° C. and stirred for 1 hour at the same temperature and another hour at ambient temperature. This mixture was added to a solution of 1,3-dibromopropane (3.92 mL, 38.6 mmol) in THF at −78° C. through an addition funnel over a period of 1.5 hours. The orange mixture was stirred at −78° C. for 2 hours, allowed to slowly warm to room temperature and kept at ambient temperature overnight (16 h). The reddish-brown mixture was quenched with water (50 mL). The aqueous layer was extracted with $Et_2O$ (5×100 mL). All organic layers were combined, washed with water (50 mL) and then brine (50 mL), and then dried over anhydrous $MgSO_4$. Concentration of the organic layer by rotary evaporator yielded 13.07 g of crude product, with a GC purity of 80% (theoretical yield based on 4,7-dimethylindene: 11.33 g; GC yield 92%). Kugelrohr distillation (130–170° C./0.2 mmHg) yielded 8.04 g (71%) of 1,3-bis(4,7-dimethyl-1-indenyl)propane. Spectroscopically pure compound was obtained through re-crystallisation from MeOH. NMR ($CDCl_3$, δ, ppm): 1.20–1.50 (m, 4H), 2.04–2.2 (m, 2H), 2.34 (s, 6H) (s, 6H), 3.50 (br d, J=9.01 Hz, 2H), 6.49 (br d, J=5.64 Hz, 2H), 6.85–6.87 (m, 4H), 6.95 (br d, J=7.63 Hz, 2H).

(1b) Synthesis of rac-1,3-propanediylbis(4,7-dimethyl-1-indenyl)$ZrCl_2$ ($PBDMIZrCl_2$) from the ligand $Li_2$ salt 4.5 g of 1,3-bis(4,7-dimethyl-1-indenyl)propane (MW 328.5 g/mol, 13.69 mmol) were dissolved in 63 ml of $Et_2O$ in a 250 ml flask equipped with stirring bar. To this solution were added dropwise at −20° C. 11.52 ml of n-BuLi 2.5 M in hexanes (28.8 mmol). At the end of the addition the white suspension was stirred for 5 hours at room temperature. 3.26 g of $ZrCl_4$ (MW 233.03, g/mol, 13.98 mmol) were slurried in 40 ml of toluene in a 50 ml flask equipped with magnetic stirrer. Both the suspensions were cooled to −20° C., and then the slurry of $ZrCl_4$ was added to the salt. The cooling bath was removed and the yellow suspension was stirred 16 hours.

After this time, the mixture was filtered; the yellow precipitate isolated (6.78 g) was dried and analysed by $^1H$ NMR spectroscopy. 6.64 g of this product were extracted with 100 ml of toluene. The organic layer was concentrated in vacuo to obtain 2.89 g of yellow powder (chemical yield 44%), wich was a mixture of 84:16 r/m-$PBDMIZrCl_2$ (by $^1H$ NMR).

EXAMPLE 2

Preparation of rac 1,3-propandiylbis(4,7-dimethyl-1-indenyl)yttrium bis trimethylsilylmethylene rac $PBDMIYCH(TMS)_2$ (2a) Preparation of $PBDMIYCl_2^-Li(THF)_2^+$(rac,meso)

1 g (MW 328.5, 3.04 mmol) of 1,3-bis(4,7-dimethyl-1-indenyl)propane was dissolved in 25 ml of anhydrous THF and cooled to −20° C. 4.2 ml (6.72 mmol) of 1.6 M n-BuLi in hexane was added in 10 min with stirring; then the mixture was allowed to reach room temperature and stirred for 4 h. A sample of this orange solution was analysed by $^1H$ NMR spectroscopy to confirm the presence of the dilithio salt of the ligand.

To this solution, cooled to −39° C., was added 0.59 g (MW 195.35, 3.04 mmol) of $YCl_3$. The suspension was allowed to reach room temperature and then stirred overnight. The solvent was evaporated under reduced pressure and the remaining light pink solid, a mixture of 2:1 rac/meso Y-chloride derivatives (by $^1H$ NMR), was extracted with 30 ml of $Et_2O$. The ether phase was concentrated and washed with 20 ml of hexane. The white powder was dried to obtain 0.38 g (20%) of product. A portion of this powder underwent several extractions with $Et_2O$ and the ratio of the isomers was improved to 85:15 in favour to the rac form. Several efforts to purify the rac isomer, by crystallisation with cooled $Et_2O$, were unsuccessful. The desired compound was determined by $^1H$ NMR.

(2b) Preparation of rac $PBDMIYCH(TMS)_2$ (rac)

0.19 g (MW 636.7, 0.30 mmol) of a mixture of 85:15 rac/meso $PBDMIYCl_2^-Li(THF)_2^+$ was suspended in 30 ml of anhydrous $EtO_2$ and cooled to −39° C. 0.06 g (MW 166.1; 0.36 mmol) of $LiCH(TMS)_2$ were added and the mixture was allowed to reach room temperature and then stirred for 2 h. No change of colour was observed during the reaction. The volatiles were removed in vacuum and the resulting white solid was extracted with 30 ml of hexane. The hexane phase was concentrated to yield 0.10 g (58% from the rac/meso $PBDMIYCl_2^-Li(THF)_2^+$) of a mixture of 92:8 rac/meso $PBDMIYCH(TMS)_2$. The desired compound was determined by $^1H$ NMR.

Starting from 5.10 g (8.0 mmol) of 85:15 rac/meso $PBDMIYCl_2^-Li(THF)_2^+$ and following the same procedure was obtained 2.81 g ( 61%) of a mixture of 85:15 rac/meso-$PBDMIYCH(TMS)_2$.

A wash with 10 ml of cold hexane afforded 1.6 g of a mixture of 92:8 rac/meso isomers. The remaining 1.2 g were dissolved in 30 ml of hexane and cooled to −39° C.; after several manipulations 0.027 g of pure rac $PBDMIYCH$ $(TMS)_2$ was obtained. Because of this low yield in the purification step, it was decided to keep the mixture of 92:8 rac/meso isomers as such. Several efforts to crystallise the little amount of the pure rac $PBDMIYCH(TMS)_2$ with hexane-toluene, were unsuccessful. The desired compound was determined by $^1H$ NMR.

2c) Preparation of meso $PBDMIYCH(TMS)_2$

The above procedure was carried out with 1.29 g (2.02 mmol) of a mixture of 1:9 rac/meso $PBDMIYCl_2^-Li(THF)_2^+$(rac, meso), 50 mL of $Et_2O$ and 0.33 g (2.02 mmol) of $LiCH(TMS)_2$ The volatiles were removed in vacuum and the resulting solid was extracted twice with hexane (2×60 mL). The hexane phase was concentrated to yield 0.59 g (51%) of a mixture of 1:9 rac/meso $PBDMIYCH(TMS)_2$ (rac, meso) and washed with 20 mL of hexane. The white solid phase was dried to yield 0.33 g (29% from the starting material) of meso $PBDMIYCH(TMS)_2$.

EXAMPLE 3

Preparation of rac 1,3-propandiylbis(4,7-dimethyl-1-indenyl)scandium bis trimethylsilylmethylene rac $PBDMIScCH(TMS)_2$ (3a) Preparation of $PBDMIScCl_2^-Li(THF)_2^+$ The above procedure as described under (2a) was carried out with 0.48 g (1.47 mmol) of PBDMI, 30 mL of THF, 2 mL (3.23 mmol) of 1.6 M n-BuLi in hexane and 0.22 g (1.47 mmol) of $ScCl_3$. The solvent was evaporated under reduced pressure and the yellow solid (0.55 g) was divided into two portions. 0.30 g were extracted with 30 mL of $Et_2O$. The ether phase was concentrated and extracted with 30 mL of hexane. The solvent was removed in vacuum to yield 0.07 g (15% yield considering that using 0.55 g of crude we would have had 0.13 g of product) of rac $PBDMIScCl_2^-Li$ $(THF)_2^+$ (principally only one isomer by $^1H$ NMR spectroscopy) as yellow powder. A sample of this powder was crystallised in $Et_2O$ at −39° C. and gave yellow crystals of pure rac $PBDMIScCl_2^-Li(Et_2O)_2^+$. The desired compound was characterized by $^1H$-NMR spectroscopy.

(3b) Preparation of rac $PBDMIScCH(TMS)_2$

The above procedure was carried out with 0.25 g of rac $PBDMIScCl_2^-Li(THF)_2^+$ 30 mL of $Et_2O$ and 0.086 g (0.52 mmol) of LiCH(TMS)$_2$. The volatiles were removed in vacuum and the resulting solid was extracted with 30 mL of hexane. The hexane phase was concentrated to yield rac PBDMIScCH(TMS)$_2$ as a yellow powder. 0.032 g (10% starting from the ligand and considering that using 0.55 g of crude we would have obtained 0.07 g) of this product was recovered. The desired compound was characterized by $^1$H-NMR spectroscopy.

EXAMPLE 4

Preparation of rac/meso 1,3-propandiylbis(4,7-dimethyl-1-indenyl)luthenium bis trimethylsilylmethylene rac PBDMILuCH(TMS)$_2$ 0.11 g (0.35 mmol) of 1,3-bis(4,7-dimethyl-1-indene) propane were dissolved in 30 mL of anhydrous THF and cooled to −20° C. 0.5 mL (0.77 mmol) of 1.6 M n-BuLi in hexane were added in 10 min with stirring, and the mixture was allowed to reach room temperature and then stirred for 4 h. A sample of this solution was analysed by $^1$H NMR spectroscopy to confirm the presence of the dilithio salt of the ligand. To this solution, cooled to −39° C., was added 0.06 g (0.35 mmol) of LuCl$_3$. The suspension was allowed to reach room temperature and then stirred overnight. The solvent was evaporated under reduced pressure. The crude of the reaction showed (by $^1$H NMR spectroscopy) the presence of 3 pairs of Me signals in a ratio of 2.6:1:1 (see above procedure). The reaction mixture was suspended in 20 mL of Et$_2$O and cooled to −39° C. 0.06 g (0.35 mmol) of LiCH(TMS)$_2$ was added and the mixture was allowed to reach room temperature and then stirred for 2 h. The volatiles were removed in vacuum and the resulting solid extracted with 30 mL of hexane. The hexane phase was concentrated to yield 0.138 g (52% starting from the ligand) of a mixture of 80:20 rac/meso PBDMILuCH(TMS)$_2$. No efforts to crystallise this powder were made. The desired compound was characterized by $^1$H-NMR spectroscopy.

EXAMPLE 5

Preparation of the dimeric hydride
Synthesis of rac [PBDMIYH]$_2$

A few mg of rac PBDMIYCH(TMS)$_2$ were dissolved in 0.6 mL of C$_6$D$_6$ and transferred to a NMR tube closed with a rubber cap. 5 ml of H$_2$ was added via a syringe. The reaction was followed by $^1$H NMR spectroscopy. After 2 h at room temperature the starting material had disappeared and signals due to rac [PBDMIYH]$_2$ appeared. The desired compound was characterized by $^1$H-NMR spectroscopy.

EXAMPLE 6

Preparation of rac-1,3-propandiylbis (tetrahydroindenyl)zirconium dichloride (r-PBTHIZrCl$_2$) r-PBTHIZrCl$_2$ 1.457 g of rac-PBIZrCl$_2$ (MW 432.5 g/mol, 3.37 mmol), 150 mg of PtO$_2$ Adams' catalyst, and 50 ml of CH$_2$Cl$_2$ were placed in a 100 ml flask equipped with a magnetic agitator. The suspension was stirred few minutes at room temperature and then transferred into a 100 ml glass autoclave. 5 atm of H$_2$ were added to the autoclave, and then the mixture was let to stirred 4 hours at room temperature. After that time, a filtration on a G3 filter and several washings with CH$_2$Cl$_2$, allowed to separate the solid from the soluble layer. The organic phase was reduced to a volume of 2 ml and let to crystallize at 0° C. overnight. The white crystals were collected and dried to obtain 0.862 g (58% chemical yield) of the desired product by $^1$H NMR analysis.

EXAMPLE 7

Synthesis of meso-1,3-propanediylbis(4,7-dimethyl-1-indenyl)ZrCl$_2$ (meso-PBDMIZrCl$_2$)

a. Synthesis of 1,3-bis(3-trimethylsilyl-4,7-dimethyl-1-indenyl)propane 7.5 g of PBDMIH$_2$ (MW 328.5 g/mol, 5.0 mmol) were suspended in 12 mL of THF in a 25 mL flask equipped with stirring bar. This suspension was transferred at room temperature in a 50 mL flask containing 0.45 g of KH (MW 40.11, 11 mmol), and 4 mL of THF. At the end of the addition the thick suspension was stirred for 1.5 hours (when H2 evolution ceased): a brown solution was obtained, to which was then added dropwise at room temperature a solution of 1.4 mL of Me$_3$SiCl (MW 108.64, d 0.856, 11 mmol) in 4 mL of THF. At the end of the addition the mixture was stirred for additional 16 h. The brown milk was treated with 40 mL of water (phase separation is observed), extracted with Et$_2$O, the organic phase separated and dried over MgSO$_4$. After filtration and drying, 2.2 of orange oil were obtained (93% yield). $^1$H NMR confirms the product.

b. Synthesis of meso-1,3-propanediylbis(4,7-dimethyl-1-indenyl)ZrCl$_2$ from the ligandTMS$_2$ derivative 1.1 g of ZrCl$_4$ (MW 233.03 g/mol, 4.6 mmol), 10 mL of CH$_2$Cl$_2$ and 2.17 g of 1,3-bis(3-trimethylsilyl-4,7-dimethyl-1-indenyl)propane (MW 472.53, 4.6 mmol) were charged in a 50 mL flask: a red suspension was obtained which was stirred for 5 h at room temperature. The reaction was stopped by removing all volatiles in vacuo. The red paste was washed with pentane, to give a brown powder, that was extracted with toluene (until the residue was colourless), dried and washed with EtOH (5 mL) and Et2O (2×5 mL), dried to give a yellow powder (0.13 g, 6%) which contains ($^1$H NMR) only meso-PBDMIZrCl$_2$.

EXAMPLE 8 (comparison)

Preparation of 1,3-propandiylbis(indenyl)zirconium dichloride (8a) Synthesis of 1,3-bis(indenyl)propane 12.8 mL of indene (91% by GC, 0.1 mol) and 130 mL of THF were placed in a 250 mL flask equipped with stirring bar and dropping funnel. After cooling to −78° C., 62.6 mL of 1.6 M BuLi solution in hexane were added dropwise. At the end of the addition the reaction mixture was allowed to warm to room temperature. The so obtained dark solution was transferred into a 250 mL dropping funnel connected to a 0.5 L flask, and then added dropwise over 1 h to a solution of 10.1 g (5 mL, 0.05 mol) of 1,3-dibromopropane in 100 mL THF under vigorous stirring, while keeping the temperature of the reaction mixture in the range −70 to −75° C. throughout the addition. The cooling bath was removed and the mixture stirred overnight. 10 mL MeOH were then added and the solvents removed under reduced pressure. The obtained solid was suspended in 100 mL of a 4:1 hexane-CH$_2$Cl$_2$ mixture and passed through silica gel using the same mixture as eluent. The solvents were removed under reduced pressure and the resulting slightly yellow crystalline product was washed twice with small portions of cold ethanol and dried in vacuum. Yield 72%, purity 95.2% (G.C.).

(8b) Synthesis of 1,3-bis(3-trimethylsilyl-1-indenyl)propane

The above product was dissolved in THF and treated with 2 eq. of BuLi in hexane at −78° C. The dianion was then quenched with two eq. TMSCl and the reaction mixture stirred for some hours at room temperature, then treated with water. The product was isolated by removing the solvents under reduced pressure, dissolving in CH$_2$Cl$_2$, filtering and drying.

(8c) Synthesis of rac/meso-1,3-propanediylbis(1-indenyl)ZrCl$_2$ (r/m-PBIZrCl$_2$) from TMS 2.5 g of ZrCl$_4$ (MW 233.03 g/mol, 10.73 mmol), 40 mL of CH$_2$Cl$_2$ and 4.5 g of 1,3-bis(3-trimethylsilyl-indenyl)propane (MW 416.8, 10.73 mmol) were charged in a 100 mL flask: a dark brown suspension was obtained which was stirred for 4 h at room temperature. The reaction was stopped by removing all volatiles in vacuum. The brown powder was transferred on a frit and washed with EtOH (5 mL) and Et$_2$O (3×10 mL), dried and extracted with toluene (until the residue was colourless), the extract dried to yield a yellow powder (0.4 g, 9%) which analyses ($^1$H NMR) as 4:1 r/m-PBIZrCl$_2$.

9 Synthesis of rac-1,3-propanediylbis(1-indenyl)ZrCl$_2$ (r-PBIZrCl$_2$)

18 g of 1.3-bis(indenyl)propane (93.6% by G.C., MW 272.35 g/mol, 62 mmol) were dissolved in 480 ml of Et$_2$O in a 1 l flask equipped with a mechanical agitator. To this solution was added dropwise at 0° C. 77 ml of n-BuLi 1.6 M in hexanes (124 mmol). At the end of the addition the brown suspension was stirred for 5 hours at room temperature. 14.4 g of ZrCl$_4$ (MW 233.03 g/mol, 62 mmol) were slurried in 480 ml of pentane in a 1 l flask. After cooling to −80° C. the first suspension was added in one portion to the slurry under vigorous stirring. The cooling bath was removed and the suspension was stirred 16 hours. The yellow suspension was brought to dry in vacuo. The yellow solid was washed with 100 ml of Et$_2$O and extracted in continuous with CH$_2$Cl$_2$ for two days. At first the solvent was reduced to 15 ml; later on it was completely removed after decantation of the solid. This last was washed with CH$_2$Cl$_2$ (2×10 ml) and dried to obtain 2.6 g of yellow powder, which corresponded to the rac-PBIZrCl$_2$ (by $^1$H NMR analysis). The collected CH$_2$Cl$_2$ washings were reduced to 15 ml and let to crystallize at −20° C. overnight. The recovered crystals, 0.75 g, were also the rac-PBIZrCl$_2$. The title compound was analyzed by $^1$H NMR analysis. In total, the chemical yield was 13%.

Polymerization Tests

All manipulations of the catalytic systems, metallocenes and aluminium alkyls were carried out in dried nitrogen atmosphere.

Materials

Solvent, such as hexane, heptane and toluene, were used after drying over molecular sieves, deoxygenated and distilled over LiAlH$_4$ or aluminium tri-isobutyl. Ethylene was polymerisation grade reagent; 1-hexene was dried over alumina and distilled over LiAlH$_4$. The r-PBDMIZrCl$_2$ used was according to the laboratory preparation as described above. The r/m-PBIZrCl$_2$ used was according to the laboratory preparation as described above, constituted of a rac-meso mixture in a molar ratio of 4:1 (isomers not assigned. The major isomer is likely the rac one).

TIOA [tris-(2.4,4-tri-methyl-pentyl)aluminium, or tri-(iso-octyl)aluminum] was purchased from Witco and diluted to 1 M solution in heptane TIOA-O [tetra-(iso-octyl)alumoxane] was the reaction product between TIOA and water in heptane at the Al/H$_2$O=2 molar ratio.

TIBAO [tetra-(iso-butyl)alumoxane] was a Witco product used as a 0.9 M solution in cyclohexane.

TIBAL [tri-(iso-butyl)aluminium] was a 1 M solution in hexane.

MAO [Methyl-alumoxane] was purchased from Witco as a 10 wt. % toluene solution and dried under vacuum to a free-flowing white powder and then solved in toluene to a 1M solution.

Thermal Analysis

Calorimetric measurements were performed by using a differential scanning calorimeter DSC Mettler. The instrument is calibrated with indium and tin standards. Weighted sample (5–10 mg) was sealed into aluminium pans, heated to 200° C. and kept at that temperature for enough time (5 minutes) to allow a complete melting of all the crystallites. Successively, after cooling at 20° C./min to 0° C., the peak temperature was assumed as crystallisation temperature (T$_c$). After standing 5 minutes at 0° C., the sample was heated to 200° C. at a rate of 10° C./min. In this second heating run, the peak temperature was assumed as melting temperature (T$_m$) and the area as global melting enthalpy (ΔH$_f$).

Intrinsic Viscosity

The measurement were done in tetrahydro-naphtalene (THN) solution obtained by dissolving the polymer at 135° C. for 1 hour.

Melt Index

Melt index (M.I.) are measured at 190° C. following ASTM D-1238 over a load of:

2.16 Kg, MI E=MI$_{2.16}$.

21.6 Kg, MI F=MI$_{21.6}$.

It is then defined as melt flow ratio (MFR), the ratio: F/E=MI F/MI E=MI$_{21.6}$/MI$_{2.16}$ $^{13}$C NMR The $^{13}$C NMR spectra were recorded at 120° C. on a Bruker DPX200 spectrometer, operating at 50.323 MHz in the Fourier Transform mode. The polymer samples were dissolved in 1,1,1,2-tetrachloro-1,2-dideuteroethane (C$_2$D$_2$Cl$_4$) to give an 8% (wt./vol.) concentration. About 3000 transients were acquired with a 75° pulse and 15 seconds of delay between pulses.

The assignements were carried out as described by Randall in Macromol.Chem.Phys. 29, 201, 1989. The distribution of triads, in case of ethylene/1-hexene, are calculated by means of the following relationship:

HHH=T$_{\beta\beta}$ EHE=T$_{\delta\delta}$ HHE=T$_{\beta\delta}$ HEH=S$_{\beta\beta}$ HEE=S$_{\beta\delta}$ EEE= 0.5(S$_{\delta\delta}$+0.5$_{\gamma\delta}$)

Wherein EHE, HHE and HHH represent the sequence ethylene/1-hexene/ethylene, 1-hexene/1-hexene/ethylene and 1-hexene/1-hexene/1-hexene respectively in the copolymer. The sum of the triads is normalized to 100. With regard to the HMR nomenclature, see J. Carmen, R. A. Harrington. C. E. Wilkes, Macromolecules, 10, 537, 1977. The 1-hexene content (mol.%) in the copolymer is calculated as:

C$_6$(mol %)=H=HHH+HHE+EHE.

EXAMPLES 10 TO 15

Ethylene Polymerisations in a 200 ml Glass Reactor

A 200 ml glass autoclave, equipped with magnetic stirrer, temperature indicator and feeding line for ethylene, was purified and purged with ethylene at 35° C. 90 ml of hexane were introduced at room temperature. The catalytic system was separately prepared in 10 ml of hexane by consecutively introducing the Aluminium alkyl, water when necessary (Al/H$_2$O=2.1), and after 5 minutes of stirring, the metallocene PBDMIZrCl$_2$ dissolved in toluene (the low amount as possible). After 5 minutes stirring, the solution, was introduced into the autoclave under ethylene flow, the reactor was closed, the temperature risen to 80° C. and pressurised to 4.6 barg. The total pressure was kept constant by feeding ethylene. After 10–20 minutes, the polymerisation was stopped by cooling, degassing the reactor and the introduction of 1 ml of methanol. The polymer was washed with acidic methanol, then with methanol and dried in oven at 60° C. under vacuum. The data relating to the characterisation of the obtained polymers are reported in Table 1.

EXAMPLES 16 TO 25 (Comparison)

The general procedure described in Examples 10 to 15 was followed, except that the metallocenes indicated in Table 1 were used. The polymerisation conditions and the data relating to the obtained polymers are reported in Table 1.

EXAMPLES 26 TO 30
Ethylene co-polymerisation its a 200 ml Glass Reactor

The same procedure was applied to the synthesis of ethylene/1-hexene copolymer as in the Examples 10 to 15, but instead of hexane, a heptane/1-hexene solution was used and the polymerisation was carried out at 70° C. The data relating to the characterisation of the obtained polymers are reported in Table 2.

EXAMPLES 31 TO 32 (Comparison)

The general procedure described in Examples 26 to 30 was followed, except that the metallocenes indicated in Table 2 were used in place of r-PBDMIZrCl$_2$. The polymerisation conditions and the data relating to the obtained polymer are indicated in Table2.

EXAMPLE 33
Ethylene polymerization with rac PBDMIYCH(TMS)$_2$

This polymerisation test was performed in a 1L reactor.

The catalytic solution was prepared suspending 19.5 mg (33.95 $\mu$mol) of rac PBDMIYCH(TMS)$_2$ in 5 g of toluene. The premix solution was prepared adding 1.44 g (10 $\mu$mol) of catalytic solution to 1.35 g (2.5 mmol) of MAO (5% Al). The autoclave, filled with 350 mL of isooctane and 6 bar of ethylene, was held at 50° C. 1.35 g of MAO (5% Al), as scavenger, was injected into the autoclave. Subsequently, the premix was added. After 40 min 2.7 g (5 mmol) of MAO (5% Al) was injected into the autoclave. After 30 min no 3.56 g of catalytic solution was injected into the autoclave. After 60 min this test was stopped. A little amount of polyethylene was collected from the stirrer washed with MeOH and dried in a vacuum oven to yield 0.24 g of polymer.

EXAMPLE 34
Ethylene polymerization with rac [PBDMIYH]$_2$

A few mg of rac (PBDMIYH)$_2$, prepared in the NMR tube, were dissolved in 20 mL of toluene in a small glass autoclave. 7 bar of ethylene were added at room temperature to the autoclave under stirring. The ethylene consumption was monitored continuously during the polymerisation and refilled twice. After 30 min the polymerisation was stopped. 3.0 g of polyethylene was obtained after washing with MeOH and drying in a vacuum oven.

TABLE 1

Ethylene polymerisation

| Examples | Metallocene type | mg | $\mu$-mol | AlR$_3$ type | mmol | Al/Zr | Yield g | Activity Kg/gZrh | I.V. dl/g |
|---|---|---|---|---|---|---|---|---|---|
| 10 | r-PBDMIZrCl$_2$ | 0.1 | 0.20 | TIOA-H$_2$O | 0.23 | 1123 | 1.84 | 591.0 | 4.6 |
| 11 | " | 0.1 | 0.20 | MAOs | 0.21 | 1025 | 2.01 | 645.7 | 3.9 |
| 12 | " | 0.1 | 0.20 | TIBAO | 0.21 | 1025 | 1.26 | 404.7 | 5.3 |
| 13 | r-PBTHIZrCl$_2$ | 0.1 | 0.2 | MAO | 0.24 | 1057 | 1.66 | 481.1 | 4.4 |
| 14 | m-PBDMIZrCl$_2$ | 0.1 | 0.2 | TIOA-H$_2$O | 0.21 | 1006 | 0.69 | 221.6 | 9.8 |
| 15 | " | 0.07 | 0.14 | MAO | 0.16 | 1074 | 0.5 | 229.4 | 7.8 |
| 16 (comp.) | r-PBIZrCl$_2$ | 0.1 | 0.2 | MAO | 0.24 | 1038 | 0.96 | 273.2 | 8.1 |
| 17 (comp.) | r-EBDMIZrCl$_2$ (rac 92%) | 0.1 | 0.21 | TIOA-H$_2$O | 0.21 | 997 | 1.35 | 421.5 | 2.7 |
| 18 (comp.) | " | 0.1 | 0.21 | TIBAO | 0.22 | 1025 | 1.38 | 430.9 | 2.5 |
| 19 (comp.) | r-EBDMIZrCl$_2$ (rac 100%) | 0.1 | 0.21 | TIOA-H$_2$O | 0.23 | 1091 | 1.36 | 424.6 | — |
| 20 (comp.) | EBIZrCl$_2$ | 0.09 | 0.21 | TIOA-H$_2$O | 0.21 | 999 | 1.18 | 369.2 | 1.6 |
| 21 (comp.) | " | 0.09 | 0.21 | M-MAO | 0.21 | 995 | 1.31 | 409.8 | 1.4 |
| 22 (comp.) | " | 0.09 | 0.21 | TIBAO | 0.22 | 1027 | 0.48 | 150.2 | 1.5 |
| 23 (comp.) | PBIZrCl$_2$, rac/meso = 4 | 0.1 | 0.23 | TIOA-H$_2$O | 0.24 | 1038 | 1.04 | 295.9 | 7.1 |
| 24 (comp.) | " | 0.1 | 0.23 | MAOs | 0.24 | 1038 | 2.30 | 654.4 | 4.7 |
| 25 (comp.) | " | 0.1 | 0.23 | TIBAO | 0.23 | 1012 | 0.55 | 156.5 | 8.3 |

Polymerisation conditions: hexane, 100 ml, Al/H$_2$O = 2.1–2.2, temperature 80° C., Ptot. 4.6 bar, PpC$_2$H$_4$ 4.2 bar. Time: 10 min

TABLE 2

Ethylene/1-hexene copolymerisation

| Example | Metallocene type | mg | TIOA mmol | Al/Zr | heptane ml | 1-hexene ml | Pp C2- bar | Time min | Yield g | Activity Kg/gZr*h | I.V. dL/g | 1-C$_6$- mol. % | DSC Tm(II) ° C. | $\Delta$H J/g |
|---|---|---|---|---|---|---|---|---|---|---|---|---|---|---|
| 26 | r-PBDMIZrCl$_2$ | 0.100 | 0.23 | 1120 | 95 | 5 | 4.5 | 10 | 1.18 | 379.0 | 4.04 | 2.2 | 117.7 | 130 |
| 27 | " | 0.100 | 0.23 | 1120 | 85 | 15 | 4.4 | 10 | 1.59 | 510.7 | 2.88 | 4.7 | 103.0 | 95 |
| 28 | " | 0.100 | 0.31 | 1510 | 50 | 50 | 4.2 | 30 | 2.60 | 278.4 | 1.44 | 9.8 | 74.9 | 49 |
| 29 | r-PBTHIZrCl$_2$ | 0.1 | 0.24 | 1057 | 85 | 15 | 4.4 | 15 | 0.89 | 172 | 2.52 | 6.1 | 88.4 | 75.1 |

TABLE 2-continued

Ethylene/1-hexene copolymerisation

| | Metallocene | | TIOA | | heptane | 1-hexene | Pp C2- | Time | Yield | Activity | I.V. | 1-C$_6$- | DSC | |
|---|---|---|---|---|---|---|---|---|---|---|---|---|---|---|
| Example | type | mg | mmol | Al/Zr | ml | ml | bar | min | g | Kg/gZr*h | dL/g | mol. % | Tm(II) °C. | ΔH J/g |
| 30 | m-PBTHIZrCl$_2$ | 0.1 | 0.22 | 1050 | 85 | 15 | 4.4 | 10 | 0.46 | 147.8 | 8 | 2.5 | 108.0 | 95 |
| 31 (comp.) | r-EBDMIZrCl$_2$ | 0.100 | 0.23 | 1090 | 95 | 5 | 4.5 | 10 | 1.4 | 437.1 | 2.53 | 2.7 | 113.7 | 116 |
| 32 (comp.) | " | 0.100 | 0.23 | 1090 | 85 | 15 | 4.4 | 20 | 1.9 | 296.6 | 1.76 | 6.5 | 91.1 | 78 |

Polymerisation conditions: 200 ml glass autoclave; heptane; Al/H$_2$O = 2.07; Metallocene/Cocatalyst were aged 5 minutes at 25° C. in 10 ml of heptane; Polym. Temperature 70° C.

What is claimed is:

1. A metallocene compound of the formula (Ia):

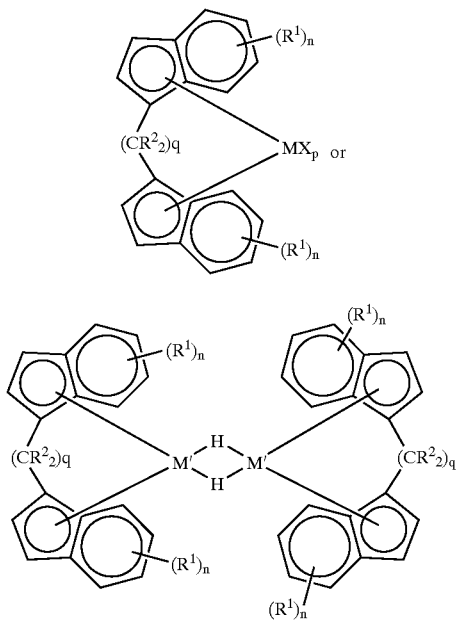

wherein
- $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;
- $R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;
- M is an atom of a transition metal selected from those belonging to group 3, 4, 5, 6 or to the lanthanide or actinide groups in the Periodic Table of the Elements;
- M' is an atom of a transition metal selected from those belonging to group 3 or to the lanthanide or actinide groups in the Periodic Table of the Elements;
- X, same or different, is a monoanionic ligand, such as a hydrogen atom, a halogen atom, an $R^4$, $OR^4$, $OSO_2CF_3$, $OCOR^4$, $SR^4$, $NR^4{}_2$ or $PR^4{}_2$ group, wherein the substituents $R^4$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing silicon or germanium atoms;
- and optionally the six-membered rings of the compounds of formula (Ia) and (Ib) are perhydrated;
- q is an integer from 3 to 5;
- n is an integer from 1 to 4, when the six-membered rings of the compound of formula (Ia) are not perhydrated, and is an integer of from 0 to 4, when the six-membered rings of the compound of formula (Ia) are perhydrated as well as in the compound of formula (Ib);
- p is an integer from 0 to 3, being equal to the oxidation state of the metal M minus two, S,S-[Ti(R,R-cyclacene)Cl$_2$] being excluded.

2. The metallocene compound according to claim 1, wherein the transition metal M of compound (Ia) is selected from the group consisting of titanium, zirconium, hafnium, yttrium and scandium.

3. The metallocene compound according to claim 2, wherein the transition metal M of compound (Ia) is zirconium.

4. The metallocene compound according to claim 1, wherein the transition metal M' is selected from Yttrium and Scandium.

5. The metallocene compound according to claim 1, wherein the X substituents are chlorine atoms or methyl groups.

6. The metallocene compound according to claim 1, wherein the substituents $R^2$ are hydrogen atoms, q is 3, n is 2 and the two $R^1$ substituents are in position 4 and 7 on the indenyl moieties.

7. The metallocene compound according to claim 1, wherein the compound is 1,3-propandiylbis(4,7-dimethyl-1-indenyl)zirconium dichloride.

8. A ligand of formula (II):

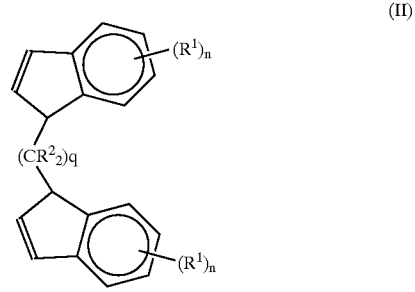

and/or its double bond isomers, wherein
- $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;

$R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;

n is an integer from 1 to 4, when the six-membered rings of the compound of formula (Ia) are not perhydrated, and is an integer of from 0 to 4, when the six-membered rings of the compound of formula (Ia) are perhydrated as well as in the compound of formula (Ib); and q is an integer from 3 to 5;

R,R-cyclacene being excluded.

9. A process for the preparation of a ligand of formula (II):

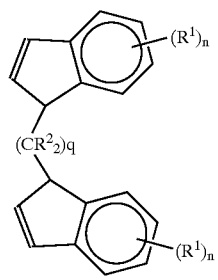

(II)

and/or its double bond isomers, wherein $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;

$R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;

n is an integer from 1 to 4, when the six-membered rings of the compound of formula (Ia) are not perhydrated, and is an integer of from 0 to 4, when the six-membered rings of the compound of formula (Ia) are perhydrated as well as in the compound of formula (Ib); and q is an integer from 3 to 5; R,R-cyclacene being excluded comprising the following steps:

contacting a compound of formula (III):

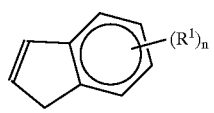

(III)

and/or its double bond isomers, wherein $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms; and n is an integer from 1 to 4, when the six-membered rings of the compound of formula (Ia) are not perhydrated, and is an integer of from 0 to 4, when the six-membered rings of the compound of formula (Ia) are perhydrated as well as in the compound of formula (Ib);

with a compound of general formula $(CR^2)_q Z_2$, wherein $R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;

q is an integer from 3 to 5;

and Z is a halogen atom, in the presence of a base.

10. The process according to claim 9, wherein said base is selected from the group consisting of hydroxides and hydrides of alkali- and earth-alkali metals, metallic sodium and potassium and organometallic lithium salts.

11. The process according to claim 10, wherein said base is n-butyllithium.

12. The process according to claim 9, wherein said halogen atom Z is a bromine atom.

13. A process for the preparation of a metallocene compound of formula (Ia):

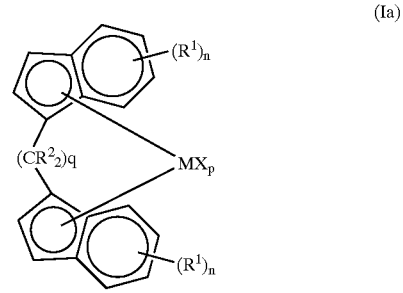

(Ia)

wherein $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;

$R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;

M is an atom of a transition metal selected from those belonging to group 3, 4, 5, 6 or to the lanthanide or actinide groups in the Periodic Table of the Elements;

M' is an atom of a transition metal selected from those belonging to group 3 or to the lanthanide or actinide groups in the Periodic Table of the Elements;

X, same or different, is a monoanionic ligand, such as a hydrogen atom, a halogen atom, an $R^4$, $OR^4$, $OSO_2CF_3$, $OCOR^4$, $SR^4$, $NR^4_2$ or $PR^4_2$ group, wherein the substituents $R^4$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing silicon or germanium atoms;

and optionally the six-membered rings of the compounds of formula (Ia) are perhydrated;

q is an integer from 3 to 5;

n is an integer from 1 to 4, when the six-membered rings of the compound of formula (Ia) are not perhydrated, and is an integer of from 0 to 4, when the six-membered rings of the compound of formula (Ia) are perhydrated;

p is an integer from 0 to 3, being equal to the oxidation state of the metal M minus two, S,S-[Ti(R,R-cyclacene)Cl$_2$] being excluded obtained by contacting a ligand of formula (II)

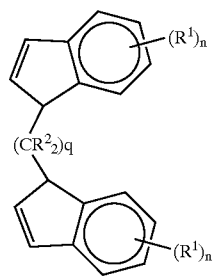

(II)

and/or its double bond isomers, wherein $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;

$R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;

n is an integer from 1 to 4, when the six-membered rings of the compound of formula (Ia) are not perhydrated, and is an integer of from 0 to 4, when the six-membered rings of the compound of formula (Ia) are perhydrated; and q is an integer from 3 to 5; R,R-cyclacene being excluded with a compound capable of forming the corresponding dianionic compound thereof and thereafter with a compound of formula $MX_{p+2}$, wherein M is an atom of a transition metal selected from those belonging to group 3, 4, 5, 6 or to the lanthanide or actinide groups in the Periodic Table of the Elements;

X, same or different, is a monoanionic ligand, such as a hydrogen atom, a halogen atom, an $R^4$, $OR^4$, $OSO_2CF_3$, $OCOR^4$, $SR^4$, $NR^4_2$ or $PR^4_2$ group, wherein the substituents $R^4$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkyl or $C_7$–$C_{20}$-arylalkyl radical, optionally containing silicon or germanium atoms; and p is an integer from 0 to 3, being equal to the oxidation state of the metal M minus two, S,S-[Ti(R,R-cyclacene)Cl$_2$] being excluded.

14. The process for the preparation of a metallocene compound of formula (Ia) according to claim 13, wherein the compound able to form said corresponding dianionic compound of formula (II) is selected from the group consisting of hydroxides and hydrides of alkali- and earth-alkali metals, metallic sodium and potassium and organometallic lithium salts.

15. The process for the preparation of a metallocene compound of formula (Ia) according to claim 14, wherein the compound able to form said corresponding dianionic compound is n-butyllithium.

16. The process for the preparation of a metallocene compound of formula (Ia) according to claim 13, wherein the compound of formula $MX_{p+2}$ is selected from titaniumtetrachloride, zirconiumtetrachloride and hafniumtetrachloride.

17. The process for the preparation of a metallocene compound of formula (Ia) according to claim 16, wherein the compound of formula $MX_{p+2}$ is zirconiumtetrachloride.

18. A process for the preparation of metallocene compounds of formula (Ib):

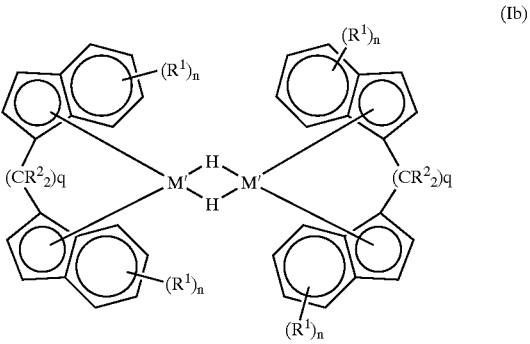

(Ib)

wherein $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;

$R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;

M is an atom of a transition metal selected from those belonging to group 3, 4, 5, 6 or to the lanthanide or actinide groups in the Periodic Table of the Elements;

M' is an atom of a transition metal selected from those belonging to group 3 or to the lanthanide or actinide groups in the Periodic Table of the Elements;

X, same or different, is a monoanionic ligand, such as a hydrogen atom, a halogen atom, an $R^4$, $OR^4$, $OSO_2CF_3$, $OCOR^4$, $SR^4$, $NR^4_2$ or $PR^4_2$ group, wherein the substituents $R^4$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing silicon or germanium atoms;

and optionally the six-membered rings of the compounds of formula (Ib) are perhydrated;

q is an integer from 3 to 5;

n is an integer from 0 to 4;

p is an integer from 0 to 3, being equal to the oxidation state of the metal M minus two, S,S-[Ti(R,R-cyclacene)Cl$_2$] being excluded comprising the following steps:

a) contacting a compound of formula (II):

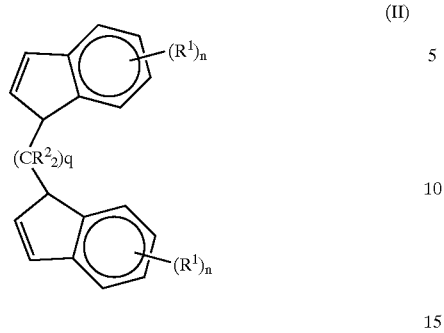

and/or its double bond isomers, wherein

R$^1$, same or different from each other, are C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radicals, optionally containing silicon or germanium atoms, and optionally two adjacent R$^1$ substituents can form a ring comprising from 5 to 8 carbon atoms;

R$^2$, same or different, are hydrogen atoms, C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl, or C$_7$–C$_{20}$-arylalkyl radicals, optionally containing silicon, germanium or halogen atoms; and optionally two adjacent R$^2$ substituents can form a ring comprising from 5 to 8 carbon atoms;

n is an integer from 0 to 4; and q is an integer from 3 to 5; R,R-cyclacene being excluded with a base selected from hydroxides and hydrides of alkali- and earth alkali metals, metallic sodium and potassium and organic lithium compounds, wherein the mole ratio between said base and the compound of formula (II) is at least 2;

b) contacting the product obtained under a) with a compound of formula (IV) M'X$_3$, wherein M' is an atom of a transition metal selected from those belonging to group 3 or to the lanthanide or actinide groups in the Periodic Table of the Elements;

and X is a halogen atom, in the presence of a polar aprotic solvent selected from dimethoxyethane, diethylether, tetrahydrofurane, toluene and dichloromethane;

c) treating the obtained product with a compound of formula M"CH(TMS)$_2$, M" being an alkali metal; and subsequently d) treating the product of step c) in a stream of hydrogen.

19. The process according to claim 18, wherein the base as used in step a) is n-butyllithium.

20. The process according to claim 18, wherein the compound of formula (IV) is ScCl$_3$ or YCl$_3$.

21. The process according to claim 18, wherein the polar aprotic solvent used in step b) is tetrahydrofurane.

22. The process according to claim 18, wherein the compound of formula M"CH(TMS)$_2$ is selected from LiCH(TMS)$_2$, NaCH(TMS)$_2$ and KCH(TMS)$_2$.

23. A catalyst for the polymerisation of olefins obtained by contacting:

(A) a metallocene compound of formula (Ia):

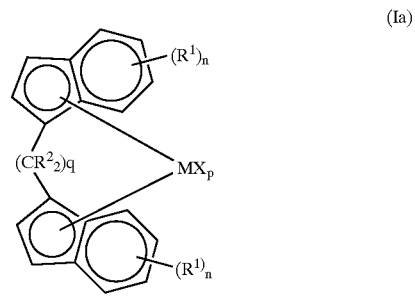

wherein

R$^1$, same or different from each other, are C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radicals, optionally containing silicon or germanium atoms, and optionally two adjacent R$^1$ substituents can form a ring comprising from 5 to 8 carbon atoms;

R$^2$, same or different, are hydrogen atoms, C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl, or C$_7$–C$_{20}$-arylalkyl radicals, optionally containing silicon, germanium or halogen atoms; and optionally two adjacent R$^2$ substituents can form a ring comprising from 5 to 8 carbon atoms;

M is an atom of a transition metal selected from those belonging to group 3, 4, 5, 6 or to the lanthanide or actinide groups in the Periodic Table of the Elements;

M' is an atom of a transition metal selected from those belonging to group 3 or to the lanthanide or actinide groups in the Periodic Table of the Elements;

X, same or different, is a monoanionic ligand, such as a hydrogen atom, a halogen atom, an R$^4$, OR$^4$, OSO$_2$CF$_3$, OCOR$^4$, SR$^4$, NR$^4_2$ or PR$^4_2$ group, wherein the substituents R$^4$ are a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radical, optionally containing silicon or germanium atoms;

and optionally the six-membered rings of the compounds of formula (Ia) are perhydrated;

q is an integer from 3 to 5;

n is an integer from 1 to 4, when the six-membered rings of the compound of formula (Ia) are not perhydrated, and is an integer of from 0 to 4, when the six-membered rings of the compound of formula (Ia) are perhydrated;

p is an integer from 0 to 3, being equal to the oxidation state of the metal M minus two, S,S-[Ti(R,R-cyclacene)Cl$_2$] being excluded; and (B) at least one of an alumoxane and a compound able to form an alkyl metallocene cation.

24. The catalyst according to claim 23, characterised in that said alumoxane is obtained by contacting water with an organo-aluminium compound of formula AlR$^5_3$ or Al$_2$R$^5_6$, wherein the R$^5$ substituents, same or different from each other, are hydrogen atoms, halogen atoms, C$_1$–C$_{20}$-alkyl, C$_3$–C$_{20}$-cyclalkyl, C$_6$–C$_{20}$-aryl, C$_7$–C$_{20}$-alkylaryl or C$_7$–C$_{20}$-arylalkyl, optionally containing silicon or germanium atoms.

25. The catalyst according to claim 23, wherein the molar ratio between the aluminium and water is in the range of 1:1 and 100:1.

26. The catalyst according to claim 23, wherein said alumoxane is selected from methylalumoxane (MAO), isobutylalumoxane (TIBAO), 2,4,4-trimethylpentylalumoxane (TIOAO), 2,3-dimethylbutylalumoxane (TDMBAO) and 2,3,3-trimethylbutylalumoxane (TTMBAO).

27. The catalyst according to claim 23, wherein the compound capable of forming a metallocene alkyl cation is a compound of formula $T^+D^{31}$, wherein $T^+$ is a Brønsted acid, able to give a proton and to react irreversibly with a substituent X of the metallocene of formula (Ib)

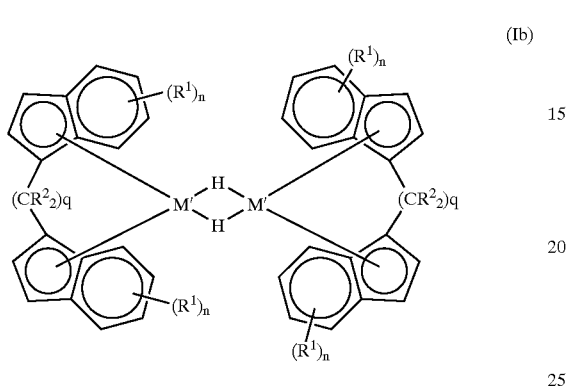

(Ib)

wherein
- $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;
- $R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;
- M is an atom of a transition metal selected from those belonging to group 3, 4, 5, 6 or to the lanthanide or actinide groups in the Periodic Table of the Elements;
- M' is an atom of a transition metal selected from those belonging to group 3 or to the lanthanide or actinide groups in the Periodic Table of the Elements;
- X, same or different, is a monoanionic ligand, such as a hydrogen atom, a halogen atom, an $R^4$, $OR^4$, $OSO_2CF_3$, $OCOR^4$, $SR^4$, $NR^4_2$ or $PR^4_2$ group, wherein the substituents $R^4$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing silicon or germanium atoms;
- and optionally the six-membered rings of the compounds of formula (Ib) are perhydrated;
- q is an integer from 3 to 5;
- n is an integer from 0 to 4;
- p is an integer from 0 to 3, being equal to the oxidation state of the metal M minus two, S,S-[Ti(R,R-cyclacene)Cl$_2$] being excluded and $D^-$ is a compatible anion, which does not co-ordinate, which is able to stabilise the active catalytic species originating from the reaction of the two compounds, and which is sufficiently labile to be able to be removed from an olefinic substrate.

28. The catalyst according to claim 27, wherein the compound of formula $T^+D^-$ is tetrakis-pentafluorophenylborate.

29. A process for the polymerisation of olefins, which comprises the polymerisation reaction of one or more olefin monomers in the presence of a catalyst obtained by contacting:

(A) a metallocene compound of formula (Ia):

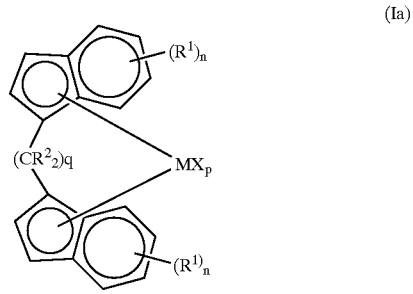

(Ia)

wherein
- $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;
- $R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;
- M is an atom of a transition metal selected from those belonging to group 3, 4, 5, 6 or to the lanthanide or actinide groups in the Periodic Table of the Elements;
- M' is an atom of a transition metal selected from those belonging to group 3 or to the lanthanide or actinide groups in the Periodic Table of the Elements;
- X, same or different, is a monoanionic ligand, such as a hydrogen atom, a halogen atom, an $R^4$, $OR^4$, $OSO_2CF_3$, $OCOR^4$, $SR^4$, $NR^4_2$ or $PR^4_2$ group, wherein the substituents $R^4$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing silicon or germanium atoms;
- and optionally the six-membered rings of the compounds of formula (Ia) are perhydrated;
- q is an integer from 3 to 5;
- n is an integer from 1 to 4, when the six-membered rings of the compound of formula (Ia) are not perhydrated, and is an integer of from 0 to 4, when the six-membered rings of the compound of formula (Ia) are perhydrated;
- p is an integer from 0 to 3, being equal to the oxidation state of the metal M minus two, S,S-[Ti(R,R-cyclacene)Cl$_2$] being excluded; and (B) at least one of an alumoxane and a compound able to form an alkyl metallocene cation.

30. A process for the polymerisation of olefins, which comprises the polymerisation reaction of one or more olefin monomers in the presence of a metallocene of formula (Ib):

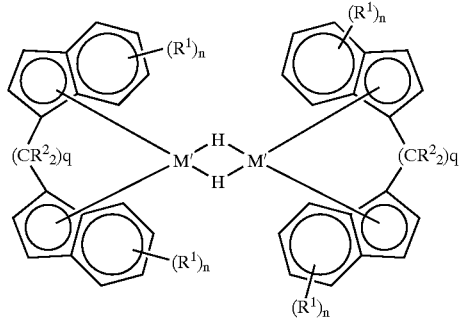

(Ib)

wherein

- $R^1$, same or different from each other, are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals, optionally containing silicon or germanium atoms, and optionally two adjacent $R^1$ substituents can form a ring comprising from 5 to 8 carbon atoms;
- $R^2$, same or different, are hydrogen atoms, $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, or $C_7$–$C_{20}$-arylalkyl radicals, optionally containing silicon, germanium or halogen atoms; and optionally two adjacent $R^2$ substituents can form a ring comprising from 5 to 8 carbon atoms;
- M is an atom of a transition metal selected from those belonging to group 3, 4, 5, 6 or to the lanthanide or actinide groups in the Periodic Table of the Elements;
- M' is an atom of a transition metal selected from those belonging to group 3 or to the lanthanide or actinide groups in the Periodic Table of the Elements;
- X, same or different, is a monoanionic ligand, such as a hydrogen atom, a halogen atom, an $R^4$, $OR^4$, $OSO_2CF_3$, $OCOR^4$, $SR^4$, $NR^4_2$ or $PR^4_2$ group, wherein the substituents $R^4$ are a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing silicon or germanium atoms;
- and optionally the six-membered rings of the compounds of formula (Ib) are perhydrated;
- q is an integer from 3 to 5;
- n is an integer from 0 to 4;
- p is an integer from 0 to 3, being equal to the oxidation state of the metal M minus two, S,S-[Ti(R,R-cyclacene)Cl$_2$] being excluded optionally in the presence of a suitable cocatalyst.

31. The process according to claim 29 or 30, wherein the olefin monomer is selected from at least one of ethylene and a $C_3$–$C_{10}$ alpha-olefin comonomer.

32. The process according to claim 31, wherein the olefin monomers are at least one of ethylene and propylene.

33. The process according to claim 29, wherein the molar ratio between the aluminium and the metal of the metallocene compound is comprised between 10:1 and 20000:1.

34. The process according to claim 29 or 30, wherein said process is carried out at a temperature comprised between 0 and 250° C. and at a pressure comprised between 0.5 and 100 bar.

35. The process according to claim 29 or 30, wherein said process is used for the preparation of homo- and copolymers of ethylene.

* * * * *

UNITED STATES PATENT AND TRADEMARK OFFICE
CERTIFICATE OF CORRECTION

PATENT NO. : 6,433,203 B1
DATED : August 13, 2002
INVENTOR(S) : Dall'occo et al.

It is certified that error appears in the above-identified patent and that said Letters Patent is hereby corrected as shown below:

Column 29,
Line 6, change "$T^+D^{31}$" to -- $T^+D^-$ --.

Signed and Sealed this

Fourth Day of January, 2005

JON W. DUDAS
*Director of the United States Patent and Trademark Office*